United States Patent [19]

Luque

[11] Patent Number: 4,790,297
[45] Date of Patent: Dec. 13, 1988

[54] SPINAL FIXATION METHOD AND SYSTEM

[75] Inventor: Eduardo R. Luque, De Las Aeoilas, Mexico

[73] Assignee: Biotechnology, Inc., Memphis, Tenn.

[21] Appl. No.: 77,440

[22] Filed: Jul. 24, 1987

[51] Int. Cl.$^4$ .............................................. A61F 5/00
[52] U.S. Cl. ................................ 128/69; 128/92 YM; 128/92 YF
[58] Field of Search ........ 128/92 YC, 92 YD, 92 YE, 128/92 YF, 92 YM, 92 YP, 92 VK, 92 V, 92 VD, 92 R, 92 Z, 92 Y, 92 YK, 92 YV

[56] References Cited

U.S. PATENT DOCUMENTS

| | | | |
|---|---|---|---|
| 2,242,003 | 5/1941 | Lorenzo | 128/92 YV |
| 2,526,959 | 10/1950 | Lorenzo | 128/92 YV |
| 3,367,326 | 2/1968 | Frazier | 128/92 VD |
| 4,611,581 | 9/1986 | Steffee | 128/69 |
| 4,653,481 | 3/1987 | Howland et al. | 128/92 YM |
| 4,655,199 | 4/1987 | Steffee | 128/92 YM |
| 4,696,290 | 9/1987 | Steffee | 128/92 YM |

OTHER PUBLICATIONS

Ryan, M. D., Taylor, T. K., and Sherwood, A. A.=-Bolt-Plate Fixation for Auterior Spinal Fusion–Clinical Orthopaedics and Related Research, Feb., 1986.

Matthiass, H. H. and Heine, Jr.=The Surgical Reduction of Spondylolisthesis–Clinical Orthopaedics and Related Research, Feb., 1986.

Primary Examiner—Robert A. Hafer
Assistant Examiner—Charles H. Sam
Attorney, Agent, or Firm—Walker & McKenzie

[57] ABSTRACT

A method of and system for fixing one or more levels of the vertebrae of a spinal column. Elongated guide wires are provided for being inserted into the vertebrae. A rigid plate is provided for being placed over the vertebrae with the guide wires passing therethrough. Cannulated screws are provided for being inserted over the guide wires, through the plate and into the vertebrae for securing the plate to the vertebrae.

7 Claims, 7 Drawing Sheets

FIG. 16 ent invention is used for segmental
SPINAL FIXATION METHOD AND SYSTEM

BACKGROUND OF THE INVENTION

1. Field of the Invention

The present invention relates, in general, to spinal interlaminal fixation methods and systems.

2. Description of the Related Art

Segmental spinal fusion plates with bolts and nuts appeared in the medical literature in 1948 (Baker, L. D., and Hoyt, W. A., Jr.: The use of interfacet Vitallium screws in the Hibbs fusion, South Med. J. 41:419, 1948) and lumbosacral fusion results using metal plates and screws were published in 1952 (Wilson, P. D., and Straub, L. R.: Lumbosacral fusion with metallic plate fixation. In American Academy of Orthopedic Surgeons: Instructional course lectures, vol. 9, Ann Arbor, 1952, J. W. Edwards). Successful clinical results using metal hardware for spinal fusions and corrections of scoliotic curves were reported in 1962 (Harrington, P. R.: Treatment of scoliosis. Correction and internal fixation by Spine instrumentation, J. Bone Joint Surg. 44-A:591, 1962). Orthopedic Equipment Company, Inc. of Bourbon, Ind. has marketed a spinal fusion system under the mark "SMo Meurig Williams Spinal Fusion" or the like, including an elongated plate having a pair of slots therein and having serrations along each edge thereof, and including serrated washers and nuts with bolts matching the serrations in the plate to inhibit longitudinal movement in the slotted plate. None of the above systems and methods disclose or suggest the present invention.

SUMMARY OF THE INVENTION

The present invention is directed toward providing an improved method and system for spinal interlaminal fixation and the like.

The spinal fixation method of the present invention comprises, in general, the steps of exposing at least a portion of the vertebrae of a spinal column; introducing at least a spaced pair of guide wires into the vertebrae; X-raying the vertebrae to confirm the position of the guide wires in the vertebrae; introducing a cannulated screw tap over the guide wires to cut screw threads into the vertebrae along the guide wires to a desired depth; placing a rigid plate over the vertebrae with the guide wires passing through the plate; and introducing cannulated screws over the guide wires and into the threads cut into the vertebrae to secure the plate to the vertebrae.

The spinal fixation system of the present invention comprises, in general, a substantially rigid, elongated plate means having one or more openings therethrough; and a plurality of screw means for extending through one of the openings in the plate means and into the vertebrae for attaching the plate means to the vertebrae, each of the screw means having an aperture extending along the longitudinal axis thereof for allowing a guide wire to extend therethrough into the vertebrae.

One objective of the present invention is to provide a spinal fixation method and system which allows direct screw fixation to the vertebral bodies to produce the potential for a very stable fusion. Blunt guide wires inserted into the pedicles help preclude penetration of the anterior cortex while permitting more accurate screw placement with the assistance of X-ray imaging.

Another objective of the present invention is to provide a spinal fixation method and system which helps reduce slippage while allowing the vertebrae to be held in better alignment in spondylolisthesis.

Another objective of the present invention is to provide a spinal fixation method and system which provides improved screw fixation to enable more effective fusions to be obtained in arthritic soft bone.

Another objective of the present invention is to provide a spinal fixation method and system with bendable plates which allows the normal lordotic curve to be maintained, as compared to some systems that straighten the spinal column abnormally.

Another objective of the present invention is to provide a spinal fixation method and system which offers a stable means for a surgical correction and provides an improved method for heavy patients who are not candidates for casts, braces or other popular conventional surgical devices.

Another objective of the present invention is to provide a spinal fixation method and system which, in severe stenosis and arthritis of the facet joints, allows the vertebral bodies to be distracted to keep the foramen open and thereby help eliminate nerve pinching.

DESCRIPTION OF THE PREFERRED EMBODIMENT

Figure 1:
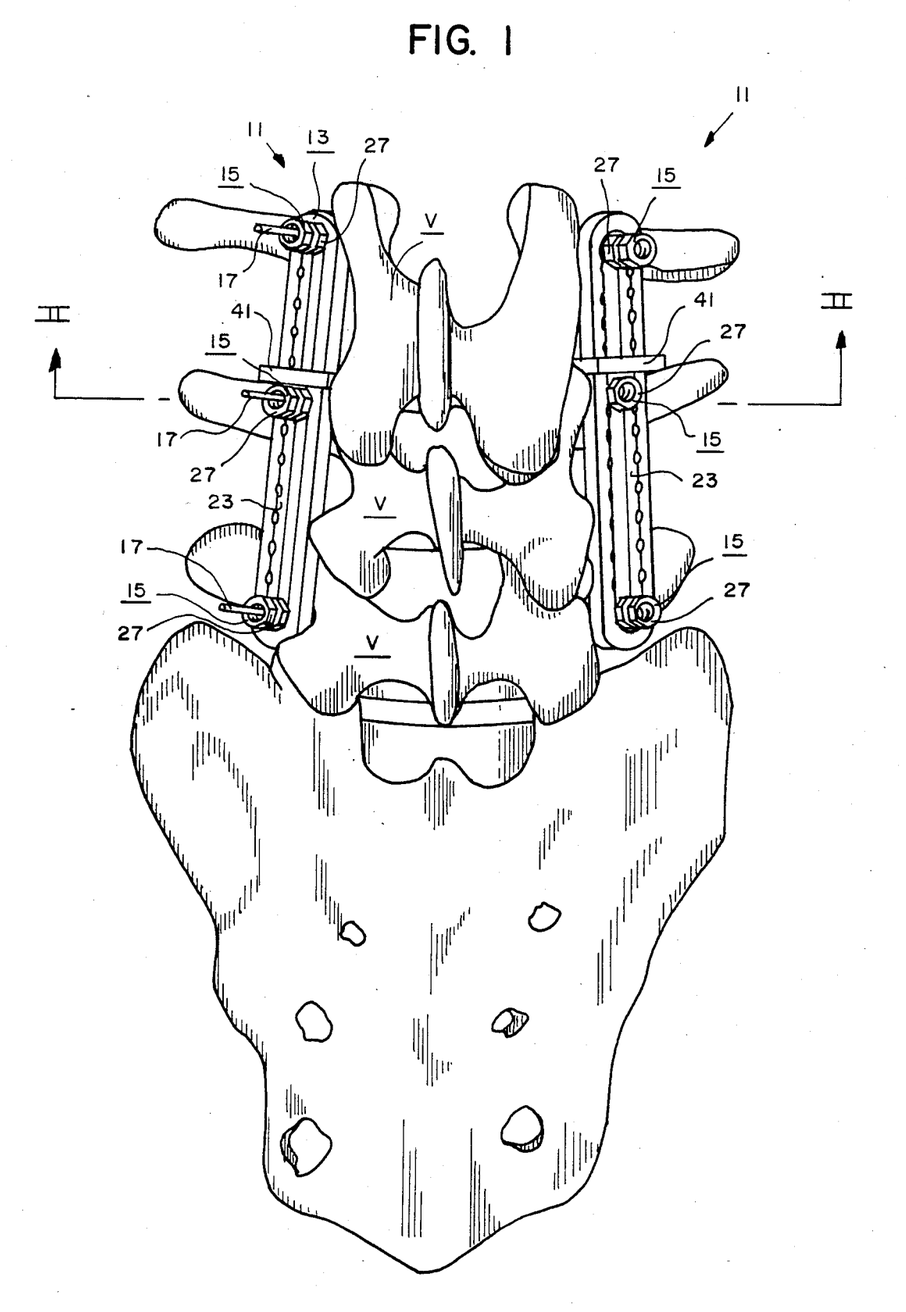
FIG. 1 is a pictoral plan view of a portion of a person's spinal column with a pair of the spinal fixation systems of the present invention secured thereto.

The preferred embodiment of the spinal fixation system 11 of the present invention is used for segmental fixation of the vertebrae V of a spinal column and comprises, in general, a substantially rigid spinal plate means or plate 13 and at least a pair of pedicule screw means or screws 15. An elongated, blunt guide wire means or guide wire 17 is preferably included to insure proper placement of each screw 15. Typically, a fixation system 11 is utilized on each side of the spinal column as shown in FIG. 1 and may be used to fix a plurality of levels of the spinal column as will be apparent to those skilled in the art.

Figure 7:
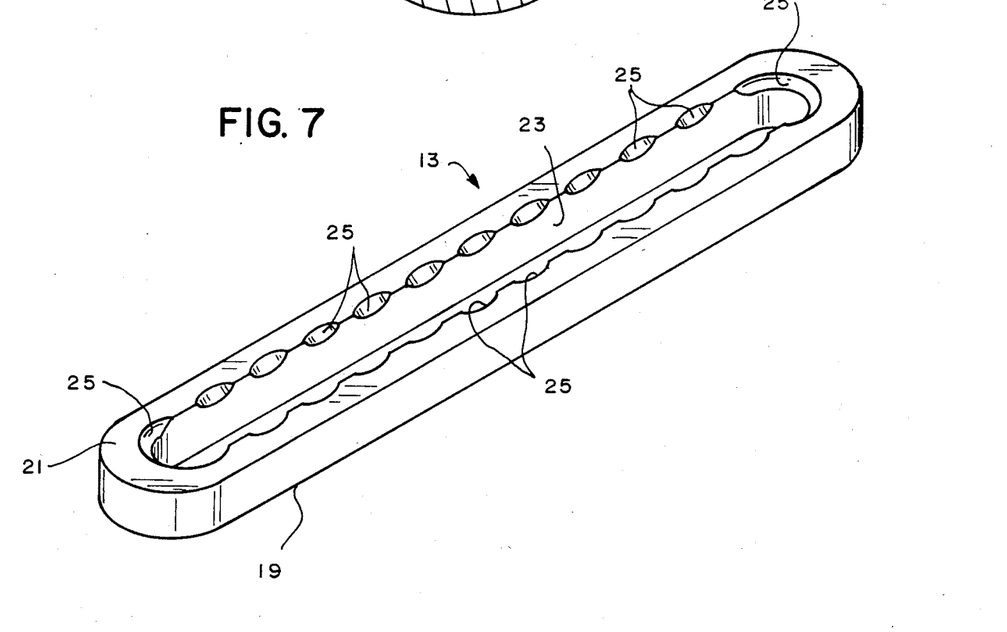
FIG. 7 is a perspective view of a plate of the spinal fixation system of the present invention.
Figure 8:
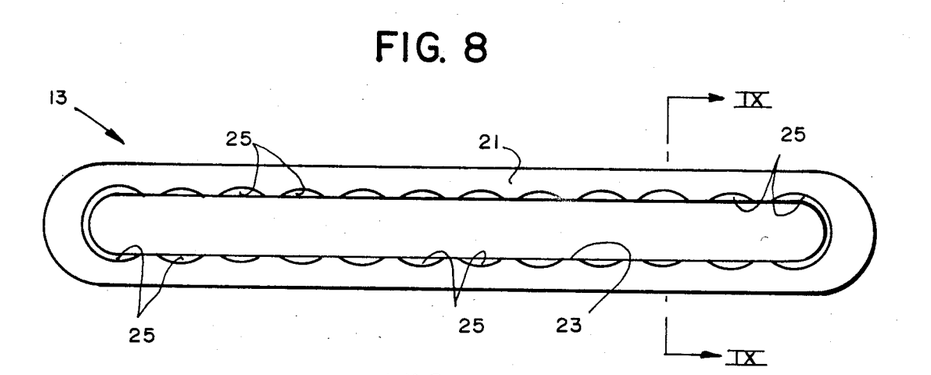
FIG. 8 is a top plan view of the plate of FIG. 7.
Figure 9:
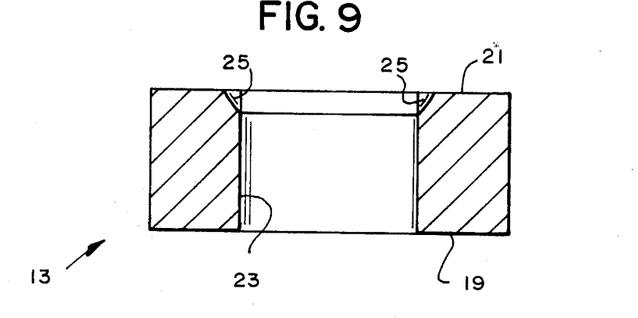
FIG. 9 is an enlarged sectional view substantially as taken on ling IX—IX of FIG. 8.

The plate 13 (see, in general, FIGS. 7-9) has a first side 19 for being directed toward the vertebrae V, a second side 21 for being directed away from the vertebrae V, and one or more openings therethrough. Preferably, the plate 13 has an elongated slot 23 extending between the first and second sides 19, 21 substantially along the longitudinal axis of the plate 13. The edge of the slot 23 adjacent the second side 21 of the plate 13 preferably has a plurality of substantially spherical, concaved depressions 25. The concaved depressions 25 are preferably positioned completely around all sides of the slot 23 in a spaced side-by-side relationship and with concaved depressions 25 on one side of the slot 23 being aligned with concaved depressions 25 on the other side of the slot 23 as clearly shown in FIGS. 7 and 8. The plate 13 may be constructed in various manners and in various sizes as will now be apparent to those skilled in the art. Thus, the plate 13 may be machined out of stainless steel in various lengths from 3 centimeters to 15 centimeters.

Figure 10:
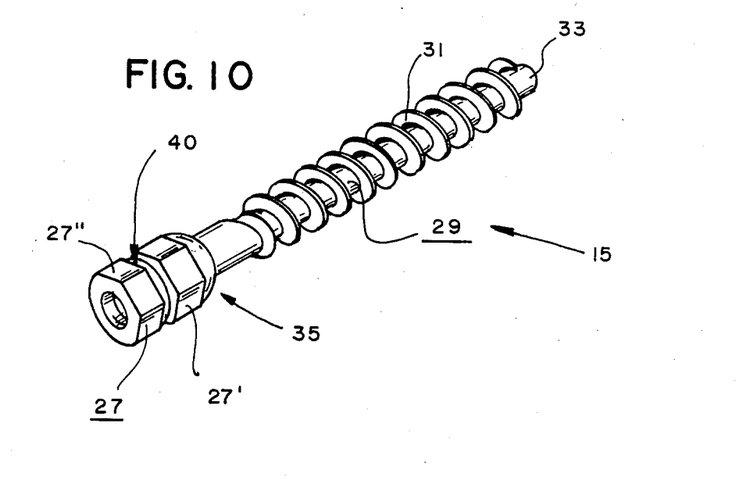
FIG. 10 is a perspective view of a screw of the spinal fixation system of the present invention.
Figure 11:
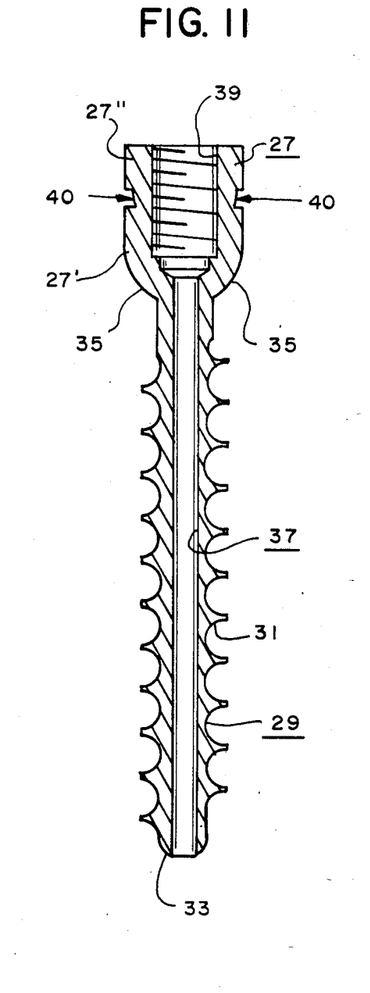
FIG. 11 is a sectional view of the screw of FIG. 10.

The screws 15 (see, in general, FIGS. 10 and 11) are sized so as to extend through the slot 23 of the plate 13 and into the vertebrae V to attach the plate 13 and vertebrae V together. The screws 15 have a head 27 and a shaft 29. The shaft 29 is preferably provided with a spongy bone helix 31 and a substantially blunt end 33. The head 27 preferably has a substantially spherical, convexed inferior or bottom surface 35 sized to fit into one or more of the concaved depressions 25 of the plate 13. The screws 15 are cannulated with an aperture 37 extending along the longitudinal axes thereof for allowing a guide wire 17 to extend therethrough. The head end portion of each aperture 37 preferably has an internally threaded portion 39. The head 27 is preferably hexagonal in cross-sectional shape and preferably has a circumferential slot 40 provided therein substantially midway between the opposite ends thereof dividing the head 27 into a lower portion 27' and an upper portion 27" and giving the head 27 a double hex arrangement. The depth of the head 27 is preferably greater than standard to provide a good grip or purchase when the screws 15 are being driven into the vertebrae V. More specifically, the depth of the head 27 is preferably approximately double the standard depth with the slot 40 dividing the head 27 into the lower and upper portions 27', 27" with each portion having a substantially standard depth. The screws 15 may be constructed in various manners and in various sizes as will now be apparent to those skilled in the art. Thus, the screws 15 may be machined out of stainless steel in various lengths from, e.g., 2.5 centimeters to 5.5 centimeters with a thread diameter between 4.5 millimeters and 6.5 millimeters.

The guide wires 17 (see FIGS. 1-5) preferably consist of substantially rigid stainless steel wire or the like having substantially blunt ends and being a calibrated or known length for being inserted into the vertebrae V in the same manner as such guide wires are now inserted into the femur. Thus, the guide wires 17 may consist of Kirschner wires, the construction and use of which are well known to those skilled in the art.

Figure 12:
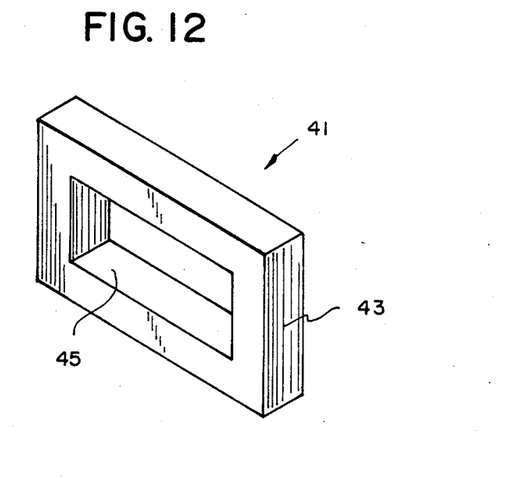
FIG. 12 is a perspective view of a plate ring means of the spinal fixation means of the present invention.
Figure 13:
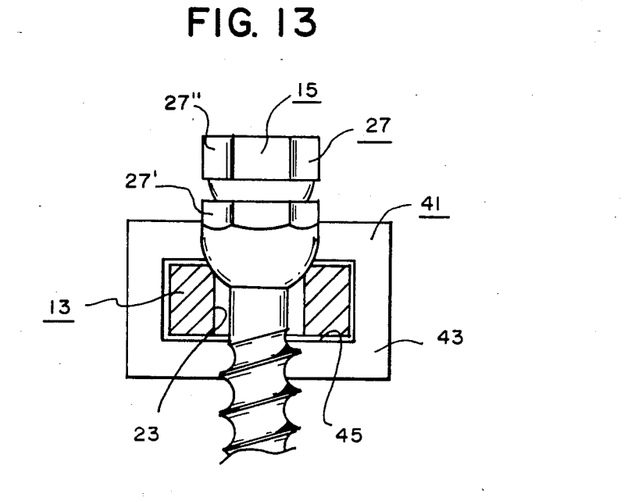
FIG. 13 is a sectional view showing the coaction between a plate, a screw and a plate ring means of the spinal fixation means of the present invention.

The system 11 preferably includes a plate ring means or plate ring 41 (see, in general, FIGS. 12 and 13) for encircling the plate 13 to prevent the plate 13 from spreading when the screws 15 are snugged down. The plate ring 41 may consist of a substantially rectangular body member 43 having a substantially rectangular slot 45 therethrough for allowing the body member 43 to slide over the plate 13. The plate ring 41 may be constructed in various manners and in various sizes as will now be apparent to those skilled in the art. Thus, the plant ring 41 may be machined out of stainless steel in a size so as to slide over the plate 13.

Figure 14:
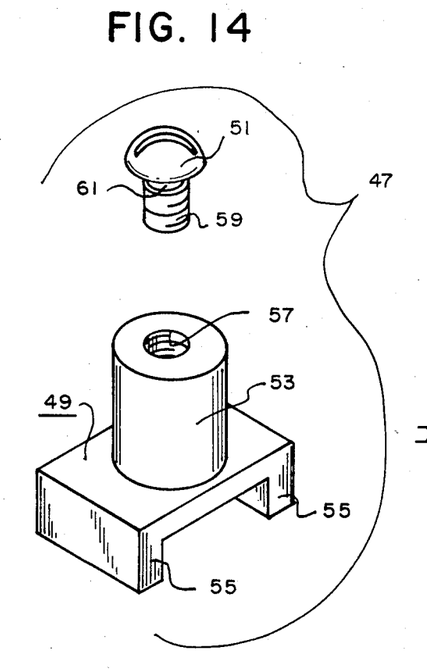
FIG. 14 is an exploded perspective view of a fixation means of the spinal fixation means of the present invention.
Figure 15:
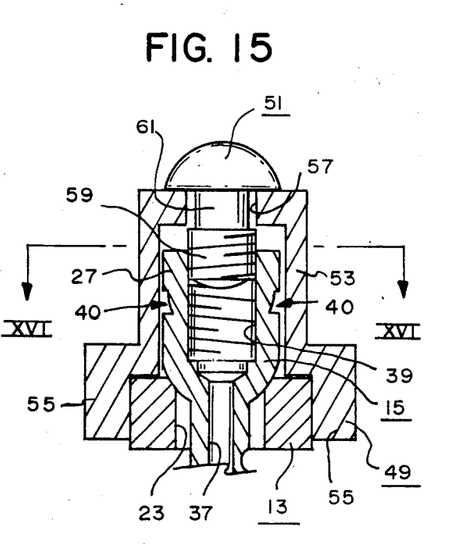
FIG. 15 is a sectional view showing the coaction between a plate, screw and fixation means of the spinal fixation means of the present invention.
Figure 16:
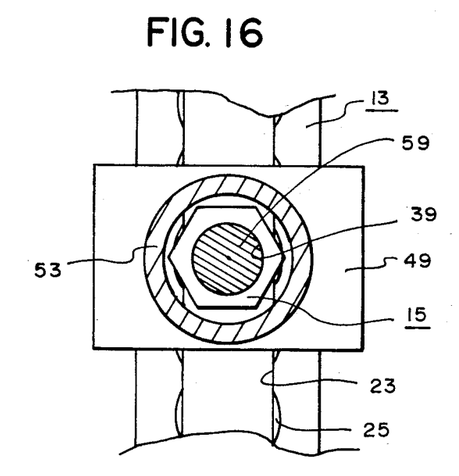
FIG. 16 is a sectional view substantially as taken on line XVI—XVI of FIG. 15.

The system 11 preferably includes fixation means 47 (see FIGS. 14-16) for selectively fixedly securing a screw 15 relative to the plate 13. The fixation means 47 preferably includes a body means or body 49 and a lock screw means or lock screw 51. The body 49 has a cup portion 53 for receiving the head 27 of a screw 15 and has a pair of flange portions 55 for selectively entrapping the plate 13 therebetween. The body 49 has an aperture 57 through the top of the cup portion 53 for allowing the shaft of the lock screw 51 to extend therethrough. The shaft of the lock screw 51 has a threaded portion 59 for engaging the threaded portion 39 of the aperture 37 through a screw 15 to thereby lock a screw 15 to the body in a manner as will now be apparent to those skilled in the art. The aperture 57 may be threaded to allow the threaded portion 59 of the shaft of the lock screw 51 to be screwed therethrough. The shaft of the lock screw 51 preferably has a non-threaded collar portion 61 for being positioned within the aperture 57 after the threaded portion 59 is screwed through the aperture 57 to rotatably secure the lock screw 51 to the body 49 and to allow the lock screw 51 to be easily screwed into the threaded portion 39 of the screw 15 as will now be apparent to those skilled in the art. The fixation means 47 may be constructed in various manners and in various sizes as will now be apparent to those skilled in the art. Thus, the body 49 and lock screw 51 may be machined out of stainless steel in sizes to fit the plate 13 and screws 15.

The surgical technique of the preferred spinal fixation method of the present invention consists first of a normal posterior midline approach to the spinal column. It is preferred that this be done by dissecting the dermis with a sharp scapel and from there on using a Bovi on six coagulation, which provides the coagulation and cutting qualities that permit an almost bloodless subperiosteal dissection to the spinous process through the entire posterior vertebral elements up to the tip of the transverse process bilaterally. After the exposure, bony or soft tissue correction may be done to overcome any pathology.

Once all usual exposure and orthopedic procedures for alignments, decompression, shortening, etc., have been done, decortication of the junction of the facet and the transverse process exposes the posterior limit of the pedicle. A 3-0 curette is used to take away the cancellous bone down to the interior cortex of the pedicle.

As a safety feature, a plurality of guide wires 17 are introduced through the cancellous bone. The guide wires 17 are expected to deflect if directed against the cortical bone. This perforation of the soft bone of the pedicle is always done under direct vision and introduced into the middle of the vertebral body. Once all guide wires 17 are in place, P/A and Lateral X-rays are taken to confirm the position of the guide wires 17 into the pedicle and into 50% to 80% of the vertebral body.

A canulated screw tap 63 is then introduced over the guide wires 17 and through the pedicle to form a threaded aperture 64 in the vertebrae V as will now be apparent to those skilled in the art. The screw tap 63 is then removed and the site is checked to insure that the pedicular cortex remains unmolested and the guide wires 17 have not advanced, etc. If any guide wire 17 is bent or deformed, it must be removed and replaced with a straight guide wire 17 (passing the screw tap 63 or screw 15 over a bent guide wire 17 could cause the guide wire 17 to advance an undesirable distance).

The tapping depth of the screw tap 63 should not be any more than the depth of the pedicle. Normally, the tap 63 should not enter the vertebral body. When tapping the sacrum, the cortex should be penetrated.

With all the guide wires 17 aligned, the appropriate size plate 13 is then placed over the guide wires 17 so that all the guide wires 17 pass through the slot 23. Note: if necessary, the plate 13 should be pre-bent to maintain the normal lordotic curve. When more than three screws 15 are to be used with a single plate 13, a plate ring 41 is passed over the plate 13 prior to placing the plate 13 over the guide wires 17 to prevent the screws 15 from spreading the slot 23 open when snugged down. The screws 15 are then introduced over the guide wires 17 through the slot 23 in the plate 13 and into the pre-tapped pedicule. A driver 65 is then used to drive the screws 15 into the pedicule. All screws 15 are inserted into 50% of the vertebral body. Prior to seating the screws 15 into the plate 13, adjustments for lordosis, kyphosis compression or distraction are done with clamps or with a joy stick action with the driver 65 on the screws 15, individually and segmentally.

The length of the screw 15 to be used is determined by measuring the exposed length of guide wire 17 and subtracting that amount from a predetermined amount (e.g., 3 and ½ inches) based on the overall length of the guide wire 17 as will now be apparent to those skilled in the art.

When adequate correction and alignment is obtained, the screws 15 are snugged down onto the corresponding concaved depressions 25 of the plate 13, each screw 17 fitting at the appropriate place and fixed firmly at the desired position. The guide wires 17 are then removed. The concaved depressions 25 and convexed bottom surfaces 35 coact to allow a screw 15 to fit the plate 13 at several angles to accommodate for abnormal pedicle positions and to be seated at 30 degrees to the plate 13, if necessary. The plate 13 is designed so that the screws 15 can slide from one concaved depression 25 to another so as to produce the desired correction before the screws 15 are seated on the plate 13.

Figure 2:
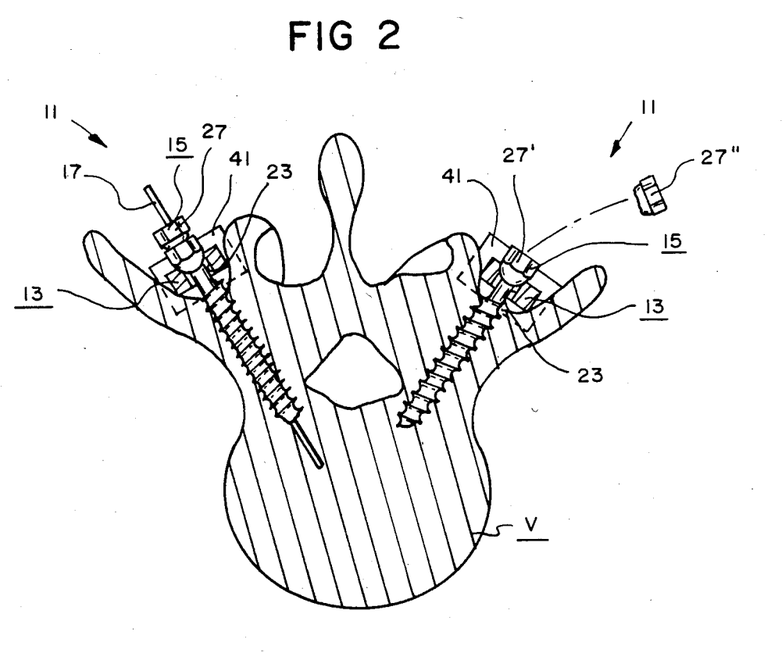
FIG. 2 is a sectional view substantially as taken on line II—II of FIG. 1.
Figure 3:
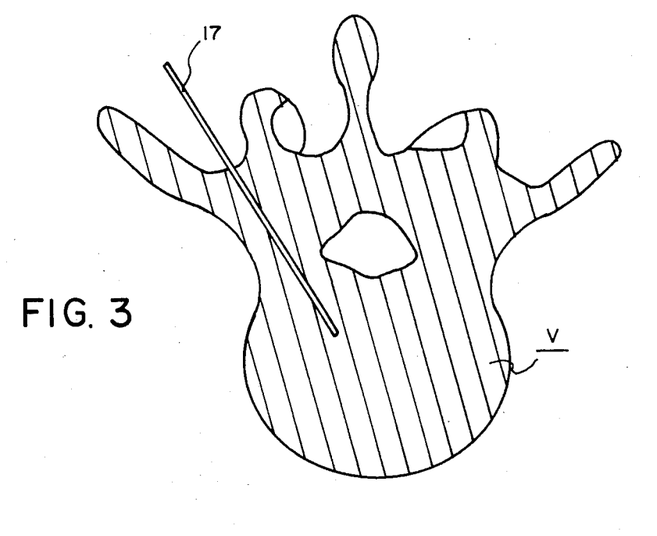
FIG. 3 is a sectional view of a vertebrae showing a guide wire being inserted thereinto.
Figure 4:
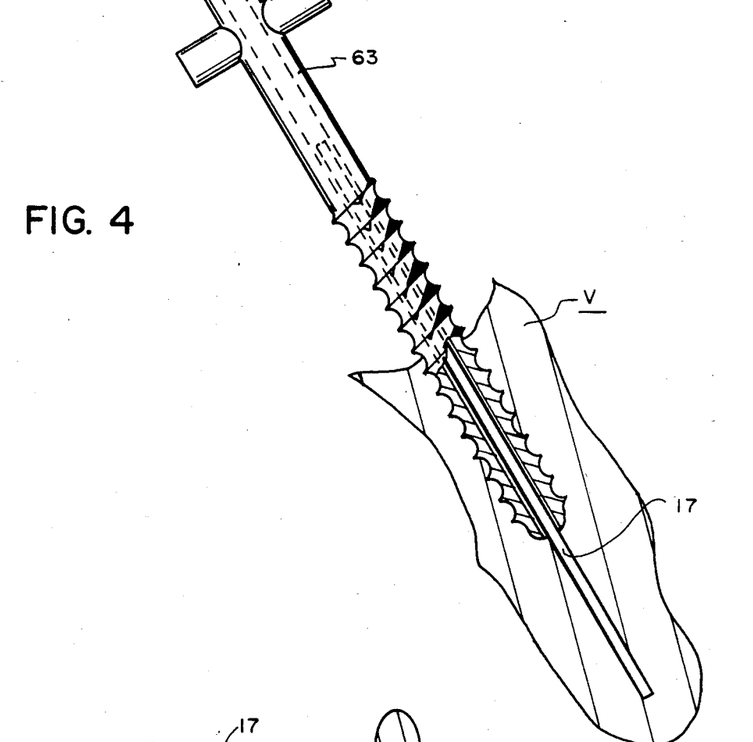
FIG. 4 is an enlarged view of a portion of FIG. 3 showing a tap being inserted over the guide wire.
Figure 5:
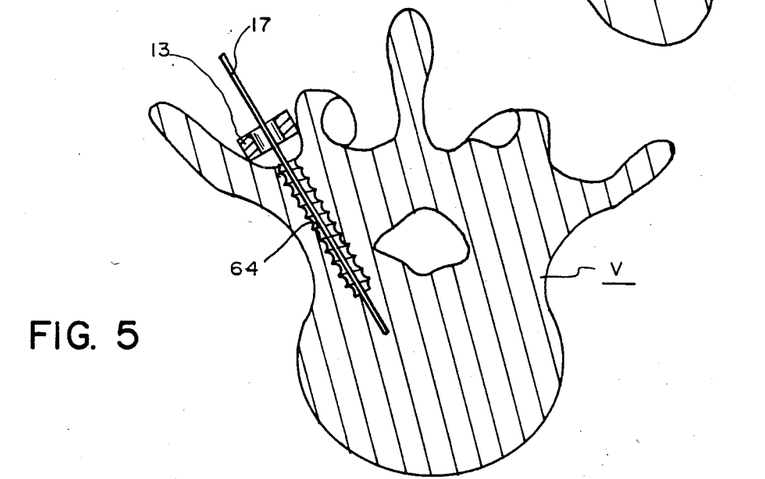
FIG. 5 is a sectional view similar to FIG. 3, but with a threaded aperture formed around a portion of the guide wire and with a plate placed over the guide wire.
Figure 6:
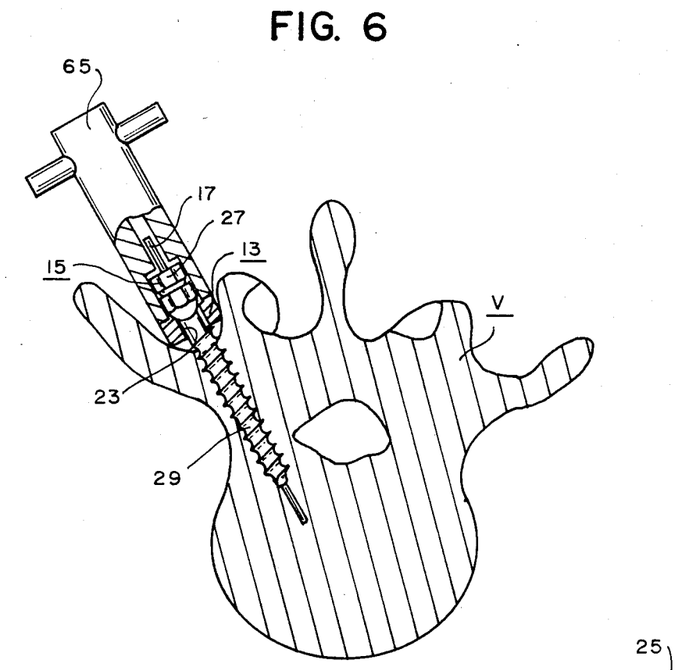
FIG. 6 is a section view similar to FIG. 5, but with a screw being inserted into the threaded aperture.

If desired, depending on the patient's muscle structure, etc., the upper portion 27" of the head 27 of each screw 15 may be broken away from the remainder of each screw 15 after the respective screw is smugged down to thereby reduce the profile of the head 27 (see, in general, FIG. 2). The slot 40 will allow the upper portion 27" of the head 27 to be easily separated from the remainder of each screw 15 by merely twisting the upper portion 27" while holding the remainder of the screw 15 fixed as will now be apparent to those skilled in the art. It will be appreciated by those skilled in the art that the double hex arrangement of each head 27 will allow the driver 65 to obtain an extremely good grip or purchase on the head 27 as the screw 15 is driven into the vertebrae V.

The system 11 allows either a rigid or semi-rigid spinal fixation. Thus, with the fixation means 47, the system 11 will allow some limited movement between the "fixed" levels of the spinal column by allowing some movement of each screw 15 relative to the plate 13 via the convexed bottom surface 35 and the concaved depressions 25 to thereby provide a semi-rigid fixation. However, with the fixation means 47 in place as hereabove described, any relative movement between the respective screw 15 and plate 13 is prevented to thereby provide a rigid fixation.

Bone chips harvested from all the posterior element decortication, spinous process extirpation and facetectomies are then introduced over the decorticated transverse processes. Occasionally, additional bone might be necessary from the iliac crest or from the bone bank.

The site is then closed in planes, usually without a drain and is dressed in compression for 48 hours.

Although the present invention has been described and illustrated with respect to a preferred embodiment and a preferred use therefor, it is not to be so limited since modifications and changes can be made therein which are within the full intended scope of the invention.

I claim:

1. In a spinal fixation method including the step of first exposing at least a portion of the vertebrae of a spinal column; the improvement comprising the steps of:
   (a) introducing at least a spaced pair of guide wires directly through the cancellous portions of the portion of the vertebrae and into the middle of the vertebral body thereof leaving an exposed length of each of said guide wires extending outward thereof, at least one end of each of said guide wires being substantially blunt to help preclude penetration of the anterior cortex by said guide wires;
   (b) X-raying the vertebrae to confirm the position of said guide wires in the portion of the vertebrae;
   (c) introducing a cannulated screw tap over said guide wires to cut screw threads into the portion of the vertebrae along said guide wires to a desired depth;
   (d) placing a rigid plate over the portion of the vertebrae with said guide wires passing through said plate; and
   (e) introducing cannulated screws over said guide wires, through said plate and into the screw threads cut into the portion of the vertebrae to secure said plate thereto.

2. The method of claim 1 in which is included the step of snugging down said screws to prevent movement between said plate and said screws.

3. The method of claim 1 in which is included the step of loosely tightening said screws to allow movement between said plate and said screws.

4. The method of claim 1 in which is included the step of removing said guide wires from the portion of the vertebrae after said screws are introduced into the screw threads cut into the portion of the vertebrae.

5. The method of claim 1 in which said guide wires are introduced into the portion of the vertebrae under direct vision.

6. The method of claim 1 in which the screw threads are cut into the portion of the vertebrae to a depth of no more than the depth of the pedicle thereof.

7. The method of claim 1 in which each of said screws consists of a one-piece, integral unit having a threaded body portion for being introduced into the screw threads cut into the portion of the vertebrae and includes an enlarged head portion attached to one end of said body portion for securing said plate to said vertebrae when said body portion is introduced thereinto.

* * * * *